United States Patent
Casteel, Jr. et al.

(10) Patent No.: US 9,755,269 B2
(45) Date of Patent: *Sep. 5, 2017

(54) DODECABORATE SALT RADICAL ANION COMPOSITIONS AND METHODS FOR MAKING AND USING SUCH COMPOSITIONS

(75) Inventors: William Jack Casteel, Jr., Fountain Hill, PA (US); Sergei Vladimirovich Ivanov, Schnecksville, PA (US); Krishnakumar Jambunathan, Macungie, PA (US); Wade Hampton Bailey, III, Emmaus, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 1396 days.

This patent is subject to a terminal disclaimer.

(21) Appl. No.: 12/277,369

(22) Filed: Nov. 25, 2008

(65) Prior Publication Data

US 2009/0297925 A1 Dec. 3, 2009

Related U.S. Application Data

(60) Provisional application No. 60/991,357, filed on Nov. 30, 2007.

(51) Int. Cl.
*H01M 10/0567* (2010.01)
*H01M 10/056* (2010.01)
*C07F 5/02* (2006.01)
*H01M 10/0525* (2010.01)

(52) U.S. Cl.
CPC ......... *H01M 10/0525* (2013.01); *C07F 5/027* (2013.01); *H01M 10/0567* (2013.01)

(58) Field of Classification Search
USPC ........ 429/188–207, 324, 325, 339, 341–344; 252/62.2
See application file for complete search history.

(56) References Cited

U.S. PATENT DOCUMENTS

| | | | |
|---|---|---|---|
| 3,551,120 A | | 12/1970 | Miller et al. |
| 5,731,470 A | * | 3/1998 | Michl et al. ............... 564/9 |
| 7,311,993 B2 | * | 12/2007 | Ivanov et al. ............ 429/121 |
| 7,348,103 B2 | * | 3/2008 | Ivanov et al. ............ 429/342 |
| 2001/0038941 A1 | * | 11/2001 | Sunano ..................... 429/66 |
| 2004/0097110 A1 | | 5/2004 | Marsiglio et al. |
| 2005/0064288 A1 | | 3/2005 | Ivanov et al. |
| 2005/0227143 A1 | * | 10/2005 | Amine et al. ............ 429/188 |
| 2006/0216612 A1 | * | 9/2006 | Jambunathan et al. ... 429/326 |
| 2007/0048605 A1 | * | 3/2007 | Pez et al. ................. 429/199 |
| 2007/0189946 A1 | | 8/2007 | Ivanov et al. |
| 2008/0220335 A1 | * | 9/2008 | Casteel .................... 429/327 |

OTHER PUBLICATIONS

Dantsin, G., et al; "Advanced Electrolyte Salts with Inherent Overcharge Protection for Lithium Ion Batteries"; 208th ECS Meeting Abstracts; No. 223; Oct. 16, 2005; XP009115984.

Zhang, et al; "A Review on Electrolyte Additives for Lithium-Ion Batteries"; Journal of Power Sources; Elsevier, Amsterdam, NL; vol. 162, No. 2; Nov. 22, 2006; pp. 1379-1394; XP025084844.

Ivanov, Sergei V., et al. "Synthesis and Stability of Reactive Salts of Dodecafluoro-closo-dodecaborate(2-)," J. Am. Chem. Soc, 2003, 125, pp. 4694-4695.

Bowden, W., "Electrochemical Oxidation of Polyhedral Boron Halide Anions," J. Electrochem. Soc.: Electrochemical Science and Technology, 1982, pp. 1249-1252.

* cited by examiner

*Primary Examiner* — Maria J Laios
*Assistant Examiner* — Helen M McDermott
(74) *Attorney, Agent, or Firm* — Larry S. Zelson

(57) ABSTRACT

The disclosure relates to new compositions comprising an, $B_{12}F_xH_{12-x}^-$ anion that may be prepared chemically or electrochemically by oxidation of $B_{12}F_xH_{12-x}^{2-}$ salts. This anion can be generated electrochemically in a voltammetry experiment, or by chemically by treatment of the (2−) anions with powerful oxidants such as $XeF2$ or $NO2(+)$ salts. The new compositions can be used as 1 electron chemical oxidants and in electrochemical cells such as lithium ion batteries where their formation at elevated potential can serve to limit the upper limit of voltage during the overcharge of such a cell.

18 Claims, No Drawings

DODECABORATE SALT RADICAL ANION COMPOSITIONS AND METHODS FOR MAKING AND USING SUCH COMPOSITIONS

CROSS-REFERENCE TO RELATED APPLICATIONS

This application claims the benefit of Provisional Application No. 60/991,357, filed on Nov. 30, 2007. The disclosure of the Provisional Application is hereby incorporated by reference.

The subject matter of the instant invention is related to the following copending and commonly assigned patent application Ser. No. 10/655,476, filed Sep. 4, 2003; Ser. No. 10/924,293, filed Aug. 23, 2004; Ser. No. 11/372,907, filed Mar. 10, 2006; Ser. No. 11/197,478, filed Aug. 5, 2005 and Ser. No. 11/710,116, filed Feb. 23, 2007. The disclosure of the foregoing patent applications is hereby incorporated by reference.

BACKGROUND OF THE INVENTION

The invention relates to a novel compound that can formed by the chemical or electrochemical oxidation of a $B_{12}F_xZ_{12-x}^{2-}$ salt to obtain a compound which can be characterized as:

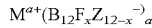

wherein a is 1 to 4 and x is at least 3, or at least 5, or at least 8, for the dodecaborate salts; $3 \leq x \leq 12$; M comprises at least one electrochemically stable cations. Z represents H, Cl, Br, or OR, where R=H, $C_{1-8}$, preferably $C_{1-3}$ alkyl or fluoroalkyl. The subscript x can be 4 to 12, 7 to 12 or 7 to 11, and mixtures of salts having x values from 4 to 12, 7 to 12 or 7 to 11. The subscripts "10–x" and "12–x" mean "10 minus x" and "12 minus x" respectively. All other subscripts with the "-" indicate a range, e.g 1-3 means 1 through 3.

The invention also relates compositions comprising the compound and to methods for making and using the compound and compositions.

Divalent salts based on the decaborate and dodecaborate closed cage structure (i.e., $B_{10}X_{10}^{2-}$ and $B_{12}X_{12}^{2-}$), are known in the art. The use of these salts has been reported in battery electrolytes, fuel cell electrolytes and other applications. Electrochemical oxidation of $B_{10}Cl_{10}^{2-}$, in acetonitrile gives a purple colored solution, (e.g., as described in Electrochemical Oxidation of Polyhedral Boron Halide Anions, Bowden, J. Electrochem Soc.; Vol 129, No. 6, Page 1249). Chemical oxidation of $B_{10}Cl_{10}^{2-}$ with $TI(CF_3COO)_3$ in acetonitrile gives a purple product which by UV-vis spectroscopy is identical to the electrochemical oxidation product of $B_{10}Cl_{10}^{2-}$. Chemical oxidation with xenon difluoride was show to form neutral $B_9Cl_9$.

Fluorinated $B_{12}$ derivatives such as $B_{12}F_xH_{12-x}^{2-}$ are described in the Cross Reference To Related Patents and Patent Applications above. It was reported (by Ivanov et. al., J. Amer. Chem. Soc., 2003, vol. 125, 4694.) that $B_{12}F_{12}^{2-}$ underwent a quasi-reversible oxidation at 4.9 V vs. Li+/0 (ca. 1.9-2.0 V vs. NHE).

There is a need in this art for oxidized radical anion products such as $B_{12}F_xZ_{12-x}^-$ or $B_{10}F_xZ_{10-x}^-$. Such products can impart desirable properties when employed alone or as additives when generated in conventional battery, capacitors or fuel cell electrolytes, or when prepared for use as reagents for carrying out chemical reactions.

BRIEF SUMMARY OF THE INVENTION

The invention solves problems associated with conventional compounds by providing a compound comprising at least one oxidized $B_{12}F_xZ_{12-x}^{2-}$ salt which can be characterized as:

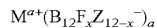

wherein a is 1 to 4 and x is at least 3, or at least 5, or at least 8, for the dodecaborate salts and; $3 \leq x \leq 12$; M comprises at least one electrochemically stable cations. Z represents H, Cl, Br, or OR, where R=H, $C_{1-8}$, preferably $C_{1-3}$ alkyl or fluoroalkyl. The subscript x can be 4 to 12, 7 to 12 or 7 to 11, and mixtures of salts having x values from 4 to 12, 7 to 12 or 7 to 11. The subscripts "10–x" and "12–x" mean "10 minus x" and "12 minus x," respectively. All other subscripts with the "-" indicate a range, e.g 1-3 means 1 through 3.

One aspect of the invention relates to a method for producing oxidized salts that can be employed for carrying out a variety of chemical oxidations by employing an oxidant. The oxidized salts can be isolated as solids or as part of oxidizing solutions for use in these applications. In another aspect of the invention, the oxidized salts can be produced by using electrochemical oxidation. Furthermore, because the oxidant is typically stable in a range of non-aqueous solvents, the oxidized salt formation at elevated potentials during charging in electrochemical cells such as lithium ion batteries or ultracapacitors, can provide a voltage limiting capability in such cells thereby preventing the cells from reaching dangerous levels of overcharge.

In another aspect of the invention relates to a method for producing a monovalent dodecaborate salt comprising: exposing a salt of the formula:

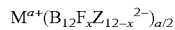

where x averages at least 4 but not more than 12 and Z represents H, Cl, Br, or OR, where R=H, $C_{1-8}$, to an oxidizing environment for a time and under conditions sufficient to form a salt of the formula:

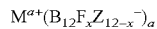

wherein a is 1 to 4; $3 \leq x \leq 12$; and M comprises at least one electrochemically stable cations.

A further aspect of the invention relates to electrolytes and electrochemical devices that incorporate the inventive salts.

DETAILED DESCRIPTION OF THE INVENTION

One aspect of the invention comprises one electron oxidants comprising monovalent dodecaborates salts of the form:

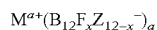 (Compound 1)

wherein x is at least 1, or at least 3 for the decaborate, or at least 5, or at least 8, for the dodecaborate salts and a is 1 to 4; $3 \leq x \leq 12$; M comprises at least one electrochemically stable cations. Z represents H, Cl, Br, or OR, where R=H, $C_{1-8}$, preferably $C_{1-3}$ alkyl or fluoroalkyl. The subscript x can be 4 to 12, 7 to 12 or 7 to 11, and mixtures of salts having x values from 4 to 12, 7 to 12 or 7 to 11. The subscripts "10–x" and "12–x" mean "10 minus x" and "12 minus x" respectively. All other subscripts with the "-" indicate a range, e.g 1-3 means 1 through 3. M is selected from electrochemically stable cations and can comprise at least one member selected from the group consisting of alkali metal, alkaline earth metal, tetraalkylammonium, or imidazolium.

In another aspect of the invention, Compound 1 may be obtained from divalent dodecaborate salts comprising those in the form:

$$M^{a+}(B_{12}F_xZ_{12-x}^{2-})_{a/2} \quad \text{(Compound 2)}$$

by electrochemical or chemical oxidation according to a process comprising:

$$B_{12}F_xZ_{12-x}^{2-} \rightarrow B_{12}F_xZ_{12-x}^{-} + e^{-}$$

or $$B_{12}F_xZ_{12-x}^{2-} + Ox \rightarrow B_{12}F_xZ_{12-x}^{-} + Ox^{-}$$

Examples of chemical oxidizers include, without limitation, nitrosyl and nitrosonium salts such as $NO^+BF_4^-$, $NO_2^+BF_4^-$, fluorine and oxidative fluorinators such as $ClF$, $ClF_3$, $BrF_3$, $XeF_2$, $K_2NiF_6$, $CeF_4$ and Ce(IV) salts, mixtures thereof, among other suitable oxidizers.

When employing electrochemical oxidation to form Compound (1), Compound (2) can be dissolved in an organic aprotic, or inorganic solvent, in a quantity ranging from about 0.1 to about 50 wt. %, provided that the solvent is not substantially oxidized by Compound (1) Examples of organic aprotic solvents comprise nitriles, including acetonitrile, propionitrile and glutaronitrile; organic carbonates and fluorinated solvents such as fluorinated organic carbonates, esters, ethers; mixtures thereof, among others. Examples of inorganic solvents comprise HF (which is protic but oxidatively stable), halogen fluorides, sulfur fluorides, chlorides, oxychlorides and oxyfluorides; mixtures thereof, among others. Typically acceptable solvents will have an oxidation potential greater than about 4.6 V vs $Li/Li^+$.

When employing chemical oxidation to form Compound (1), chemical oxidation may be carried out by reacting Compound (2) with at least one suitable oxidant in at least one solvent which either does not react with the oxidant or reacts more slowly with the oxidant than Compound (2). Examples of suitable solvents comprise at least one of HF, acetonitrile, glutaronitrile, bromine trifluoride; mixtures thereof, among others. In one example of a chemical oxidation process, Compound (2) is suspended or dissolved in the solvent and the oxidizer added at between about 0.1 and about 2 Mol equivalents relative to Compound (1). When fluorine is used as the oxidant, fluorination of any of $B_{12}F_xH_{12-x}^{2-}$ typically produces the fully fluorinated radical anion $B_{12}F_{12}^{1-}$. Without wishing to be bound by any theory or explanation it is believed that $F_2$ and similar oxidizers can fully fluorinate the partially fluorinated salts before generating the fully fluorinated radical anion.

In one aspect of the invention, the inventive salts can be used with or generated from a lithium based salt of the formula:

$$Li_2B_{12}F_xZ_{12-x}$$

wherein x is at least 1, or at least 3 for the decaborate, or at least 5, or at least 8, for the dodecaborate salts. Z represents H, Cl, Br, or OR, where R=H, $C_{1-8}$, preferably $C_{1-3}$ alkyl or fluoroalkyl. The subscript x can be 4 to 12, 7 to 12 or 7 to 11, and mixtures of salts having x values from 4 to 12, 7 to 12 or 7 to 11. The most preferred compounds are $Li_2B_{12}F_{12}$, and $Li_2B_{12}F_xZ_{12-x}$ where x is 6, 7, 8, 9, 10, 11 and 12 or where x is 7, 8, 9, 10 and 11 and mixtures of $Li_2B_{12}F_xZ_{12-x}$ where x is 6, 7, 8, 9, 10, 11 and 12 or where x is 7, 8, 9, 10 and 11. For example, a mixture of $Li_2B_{12}F_8H_4$ salt means $Li_2B_{12}F_xH_{12-x}$ where x is predominantly 8 with lesser amounts of x=6, 7, 9, 10, 11, and 12. The subscripts "10-x" and "12-x" mean "10 minus x" and "12 minus x" respectively. All other subscripts with the "-" indicate a range, e.g 1-3 means 1 through 3. Specific examples of suitable lithium fluoroborate compounds comprise at least one member selected from the group consisting of $Li_2B_{12}F_{8-12}Z_{0-4}$ where Z is Cl, Br, or OR where R is $C_{1-8}$, preferably $C_{1-3}$. Typically, the salts include $Li_2B_{10}F_{10}$, $Li_2B_{12}F_{12}$, $Li_2B_{12}F_{10-12}(OH)_{0-2}$, $Li_2B_{12}F_{10-12}(Cl)_2$, $Li_2B_{12}F_{8-10}(H)_{0-2}$, $Li_2B_{12}F_{8-12}(OCF_3)_{0-4}$, $Li_2B_{10}F_{8-10}Br_{0-2}$, $Li_2B_{12}F_5H_7$, $Li_2B_{12}F_6H_6$, $Li_2B_{12}F_7H_5$, $Li_2B_{12}F_8H_4$, $Li_2B_{12}F_9H_3$, $Li_2B_{12}F_{10}H_2$, $Li_2B_{12}F_{11}H$ and mixtures of salts with varying x such that the average x is equal to or greater than 5, or equal to 9 or 10, or $Li_2B_{12}F_xCl_{12-x}$ and $Li_2B_{12}F_xBr_{12-x}$ where x is 10 or 11. Additional details of this lithium based salt as well as electrolytes and electrochemical devices in which the inventive salt can be employed, are disclosed in U.S. patent application Ser. No. 10/924,293; hereby incorporated by reference.

In another aspect of the invention, the inventive salts and the lithium based salt can be employed with at least one additive, and in electrolytes and electrochemical devices. Examples of suitable additives can comprise at least one member selected from the group consisting of inorganic salt additives and organic additives such as LiBOB, LiBF4, among others that are disclosed in U.S. patent application Ser. No. 11/300,287; hereby incorporated by reference. The concentration of such additives in an electrolyte is normally about 0.1 to 5 wt. % based on the total weight of the electrolyte solution.

While the inventive salts can be employed in any suitable application or end-use, examples of such applications comprise usage as: i) a stable one electron oxidant, particularly of neutral species to stable reactive cations with lower oxidation potentials than those of the inventive salts, ii) an oxidative dopant in the polymerization of conductive polymers; and in iii) electrochemical devices such as a battery, fuel cell and ultracapacitor. In electrochemical cells such as batteries or ultracapacitors, the inventive salt can be added as a chemical passivating additive, or if generated in situ can serve to maintain the voltage in the cell at a safe upper limit thereby providing overcharge protection.

When the oxidized salts of this invention are generated in solution by chemical or electrochemical oxidation they are they can be prepared at concentrations ranging from about 0.001M to about 1M, or about 0.01M to about 1M, or about 0.1 to about 0.5M. The oxidized salts can be employed in such concentrations or diluted by being combined with a suitable solvent, among other components.

In a further aspect of the invention, the oxidized compound and electrolytes containing the compound are substantially free of water. By substantially free it is meant that the compound or electrolyte contains less than about 100 ppm of water and other hydroxyl moieties, and typically less than about 50 ppm of water and other hydroxyl moieties.

Certain aspects of the invention, for example, salt isolation as a solid and in a series of solutions, its characterization in solution and its quantification in solid and solution are illustrated by the following Examples which shall not limit the scope of the claims appended hereto.

Example 1

Electrochemical Oxidation of $Li_2B_{12}F_9H_3$

For the electrochemical oxidation of $Li_2B_{12}F_9H_3$ an electrochemical cell based on a 0.07 cm² glassy carbon working electrode (Bioanalytical Systems Inc.) and Li metal foil (FMC Corp.) reference and counter electrodes was fabricated. A CH Instruments CHI660a potentiostat was used as the power supply. A current of 0.14 mA was applied to ~5 mL of a 0.4 M solution of $Li_2B_{12}F_9H_3$ in ethylene carbonate/diethyl carbonate (EC/DEC) for ~1 hr. red/orange species formed underneath the working electrode, which gradually diffused into the bulk solution. Titration with thiosulfate indicated that ~0.002M of a 1 electron oxidant had been formed by electrolysis. An aliquot of the solution was loaded into a Teflon™ Harrick liquid optical cell (part # DLC2) with sapphire windows spaced 0.1 mm apart to enable full-scale observation of the absorption values without the need for dilution. The solution in the Harrick cell was analyzed by UV-visible spectroscopy on a Cary model 300 spectrophotometer from Varian, Inc. Single scans were run from 200-700 nm with a resolution of 1 nm at a scan rate of 4 nm/s. Two new absorption peaks were observed in the $Li_2B_{12}F_9H_3$ solution at 350 and 460 nm after electrochemical oxidation. The color of the solution as well as these absorption bands gradually decreased and completely disappeared after 8-9 hrs.

Comparative Example 1

UV Spectrum of $Li_2B_{12}F_{12}$

An untreated 0.4 M solution of $Li_2B_{12}F_{12}$ in EC/DEC is clear and colorless. UV-visible spectroscopy was performed on the solution as in example 1 which shows UV absorption peaks of $Li_2B_{12}F_{12}$ occurring at 290 and 315 nm.

Example 2

Electrochemical Oxidation of $Li_2B_{12}F_{12}$

A 0.4 M solution of $Li_2B_{12}F_{12}$ in EC/DEC was electrochemically oxidized by the method described in example 1. On electrochemical oxidation, a lemon-yellow species was observed under the working electrode which gradually diffused into the solution. UV-visible spectroscopy showed a new absorption peak at 410 nm in addition to the original UV absorption peaks of $Li_2B_{12}F_{12}$ at 290 and 315 nm. The color of the solution as well as the new UV-visible peak gradually decreased, completely disappearing in 24 hr. Electrolysis of solutions at 5.0V for 2 hrs gave similar results except a more deeply colored solutions were obtained which are indicative of higher concentrations of radical. Electrolysis currents were higher as expected. Mass susceptibility shift correlation (NMR and mass susceptibility balance measurements) and iodometric titrations of solutions (anhydrous LiI added to the solution in the glove box followed by aqueous thiosulfate titration) indicated about 10% conversion of $B_{12}F_{12}^{2-}$ to the radical, or 0.03-0.04 M radical anion concentration. Coulometry correlated well with the quantitation studies. The same byproducts were observed over a long time period while the radical had completely decayed (UV-Vis) by the fourth day.

Example 3

Chemical Oxidation of $K_2B_{12}F_{12}$ with Xenon Difluoride

In an Ar-filled dry box, about 500 mg (1.1 mmol) $K_2B_{12}F_{12}$ was loaded into one arm of a 2-armed FEP reactor and ~200 mg $XeF_2$ (1.2 mmol) was loaded into the other arm. On a vacuum line 3 mL of anhydrous hydrogen fluoride was distilled into each arm of the reactor thereby forming colorless solutions in each reactor arm. The $XeF_2$ solution was poured into the $K_2B_{12}F_{12}$ solution at ~0° C. Slow gas evolution was observed and a gradual yellowing of the solution. After 1 hr. gas evolution ceased and the solution was a bright lemon yellow. The HF was evacuated at 0° C. leaving a pale yellow solid. In a dry box this solid was dissolved in EC/DEC giving a yellow solution. The UV-visible spectrum showed the new absorption peak at 410 nm, in the same location as that observed for electrochemically oxidized $Li_2B_{12}F_{12}$.

Example 4

Chemical Oxidation of $(H_3O)_2B_{12}F_{12}$

In an Ar-filled dry box 5 g (11 mmol) of $(H_3O)_2B_{12}F_9H_3$ was loaded into a single arm valved FEB reactor. Approximately 20 mL of anhydrous HF was distilled into the reactor and a 20% $F_2$/80% $N_2$ stream was bubbled into the solution. Analysis of the solution by $^{19}F$ NMR after the addition of ~40 mmol $F_2$ indicated that $B_{12}F_9H_3^{2-}$ had been converted completely to $B_{12}F_{12}^{2-}$. An additional 40 mmol $F_2$ was added to the solution over which time it turned deep blue in color. Removal of residual fluorine and HF by distillation left ~6 g of pale blue solid. A sample of the solid was treated with potassium iodide and gave a deep orange solution in acetonitrile, indicative of oxidizer. Back titration of this solution with $Na_2S_2O_3$ solution was consistent with the solid consisting of 60 mol % of a one electron oxidizer. Another sample of this solid was dissolved in acetonitrile and gave rise to a pale blue solution. UV analysis of this solution showed the 410 nm absorption peak at much higher intensity than was observed for the electrochemical or $XeF_2$ chemical oxidation of $B_{12}F_{12}^{2-}$.

Example 5

Characterization of Solutions of Oxidized $Li_2B_{12}F_{12}$ by Time of Flight Secondary Ion Mass Spectrometry (ToF-SIMS)

A solution of the yellow oxidized product from example 3 was dissolved in acetonitrile and analyzed by Time of Flight Secondary Ion Mass Spectrometry (ToF-SIMS) on a PHI Trift II TOFMS instrument. In this experiment, the samples were ionized with a $^{69}Ga$ liquid metal ion gun. Positive and negative ions were analyzed via TOFMS (B3 instrument file). The data were collected with 138 ps/bin, 1.5-2000 Daltons, 5 kV post acceleration, 250 micron raster, 1.5 pA ion gun current and 1.5-5 min collection times. Under SIMS conditions, two phenomena are common: recombination of preformed ions with electrons and neighboring ions in the near surface region as well as fragmentation of ion clusters. In addition, doubly charged ion clusters are rarely maintained. For example, the neutral divalent salt $Li_2B_{12}F_{12}$ would be expected to give rise to both $B_{12}F_{12}^-$ and $LiB_{12}F_{12}^-$ ions, while the neutral, oxidized radical monovalent salt $LiB_{12}F_{12}$ would be expected produces primarily $B_{12}F_{12}^-$, but not the divalent monoanion $LiB_{12}F_{12}^-$. The ratio of $B_{12}F_{12}^-$ to $LiB_{12}F_{12}^-$ should be close to 1 for the neutral divalent salt, $Li_2B_{12}F_{12}$, which contains the divalent anion, $B_{12}F_{12}^{2-}$. This ratio is expected to be significantly higher than 1 for the neutral, oxidized salt, $LiB_{12}F_{12}$, which contains the radical monovalent anion, $B_{12}F_{12}^-$. As expected, SIMS data on the unoxidized $Li_2B_{12}F_{12}$ shows 2 primary sets of peaks centered at 358 D for $B_{12}F_{12}^-$ and 365 D for $LiB_{12}F_{12}^-$, which are approximately the same intensity. When the $Li_2B_{12}F_{12}$ salt was oxidized with xenon difluoride in acetonitrile solution and the yellow solid product mixture analyzed by SIMS, the same primary sets of peaks were observed, but the $B_{12}F_{12}^-$ peak centered at 358 D was nearly twice the intensity of the $LiB_{12}F_{12}^-$ peak centered at 365 D. This indicates that the $LiB_{12}F_{12}$ salt based on the radical anion $B_{12}F_{12}^-$ is one of the products of $XeF_2$ oxidation of $Li_2B_{12}F_{12}$.

Example 6

Characterization of Solutions of Oxidized $Li_2B_{12}F_{12}$ by EPR

A 0.4 M solution of $Li_2B_{12}F_{12}$ in 7EC/3DEC was electrochemically oxidized in an optically flat cell, part # WG-810-A available from Wilmad-Labglass, by the method described in example 1, with the exception that Pt wire working, counter and pseudo reference electrodes were used. On electrochemical oxidation, a lemon-yellow species was observed under the working electrode which gradually diffused into the solution. The solution was analyzed by EPR measurements on a Bruker ESP 580 X-Band EPR Spectrometer. A TE102 mode resonator was used at 25° C. with 100 kHz field modulation. A total of 20 scans were collected. A solution of 0.4M $Li_2B_{12}F_{12}$ in 7:3 EC-DEC was used for the experiments because it was found to promote excellent lifetimes for the generated radical. Upon electrolysis, the steady growth of at single, broad, dysonian signal at a g-factor of approximately 2.0094 was observed which is consistent with a single unpaired electron of a radical species. Ex-situ generation of the radical anion in a glove bag followed by analysis of a colored solution gave the same signal.

Comparative Example 2

EPR of Inert Supporting Electrolyte in EC/DEC

A 0.4 M solution of tetrabutylammonium hexafluorophosphate in 7EC/3DEC was electrochemically oxidized by the method described in example 6. The solution was analyzed by EPR measurements as in example 6. No EPR signals were observed.

The invention has been described with reference to certain aspects, but other aspects and embodiments are apparent to persons of skill in the art, and are included within the scope of the claims.

The invention claimed is:

1. A method for producing a composition comprising: exposing a salt of the formula:

$$M^{a+}(B_{12}F_xZ_{12-x}^{2-})_{a/2}$$

where x averages at least 4 but not more than 12 and Z represents H to a chemically oxidizing environment for a time and under conditions sufficient to form an oxidized salt of the formula:

$$M^{a+}(B_{12}F_xZ_{12-x}^-)_a$$

wherein a is 1 to 4; $4 \leq x \leq 12$; and M comprises at least one member selected from the group consisting of alkali metal, alkaline earth metal, tetraalkylammonium and imidazolium; and, combining the oxidized salt and a lithium salt of the formula:

$$Li_2B_{12}F_xZ_{12-x}$$

where x averages at least 4 but not more than 12 and Z represents H, Cl, Br, or OR, where R=H, or $C_{1-8}$.

2. The method of claim 1 wherein M comprises an alkali metal.

3. The method of claim 1 further comprising adding at least one solvent wherein the solvent comprises at least one member selected from organic aprotic solvents or inorganic solvents.

4. The method of claim 3 wherein the solvent has an oxidation potential greater than about 4.6V.

5. The method of claim 3 wherein the amount of said oxidized salt ranges from about 0.001M to about 0.5 M.

6. The method of claim 1 further comprising adding at least one member selected from the group consisting of nitriles, acetonitrile, propionitrile and glutaronitrile; organic carbonates and fluorinated solvents, fluorinated organic carbonates, esters, ethers, mixtures thereof, and aprotic gel polymers.

7. An electrolyte comprising the composition produced by the method of claim 1.

8. An electrochemical device comprising the electrolyte of claim 7.

9. The method of claim 1 wherein the composition has a UV-visible spectrum peak greater than about 400 nm.

10. The method of claim 1 wherein the composition is substantially free of water and other hydroxyl moieties.

11. The method of claim 1 wherein said chemically oxidizing environment comprises at least one member selected from the group consisting of nitrosyl, nitrosonium salts, fluorine and oxidative fluorinators.

12. The method of claim 11 wherein the chemically oxidizing environment comprises at least one member selected from the group consisting of $NO^+BF_4$ and $NO_2^+BF_4$.

13. The method of claim 11 wherein the chemically oxidizing environment comprises at least one member selected from the group consisting of ClF, $ClF_3$, $BrF_3$, $XeF_2$, $K_2NiF_6$, and $CeF_4$.

14. The method of claim 1 further comprising dissolving the salt in at least one solvent before said exposing.

15. The method of claim 14 wherein the solvent comprises at least one member selected from the group consisting of HF, acetonitrile, glutaronitrile, and bromine trifluoride.

16. The method of claim 15 wherein the chemically oxidizing environment comprises fluorine.

17. The method of claim 15 wherein the chemically oxidizing environment comprises $XeF_2$.

18. The method of claim 1 further comprising adding at least one additive selected from the group consisting of LiBOB and $LiBF_4$.

* * * * *